US00PP14356P29

(12) United States Plant Patent
Carruth

(10) Patent No.: US PP14,356 P2
(45) Date of Patent: Dec. 9, 2003

(54) HYBRID TEA ROSE PLANT NAMED 'WEKPLAGNEZE'

(50) Latin Name: *Rosa hybrida*
Varietal Denomination: WEKplagneze

(75) Inventor: Thomas F. Carruth, Upland, CA (US)

(73) Assignee: Meredith Corporation, Des Moines, IA (US)

( * ) Notice: Subject to any disclaimer, the term of this patent is extended or adjusted under 35 U.S.C. 154(b) by 60 days.

(21) Appl. No.: 10/327,733

(22) Filed: Dec. 23, 2002

(51) Int. Cl.[7] ..... A01H 5/00
(52) U.S. Cl. ..... Plt./133
(58) Field of Search ..... Plt./133, 144, 141, Plt./130

*Primary Examiner*—Bruce R. Campell
*Assistant Examiner*—Annette H. Para
(74) *Attorney, Agent, or Firm*—McKee, Voorhees & Sease, P.L.C.

(57) ABSTRACT

A new variety of Hybrid Tea rose suitable for garden decoration, having flowers of white coloration.

1 Drawing Sheet

Botanical classification: *Rosa hybrida.*

BACKGROUND OF THE INVENTION

This invention relates to a new and distinct variety of Hybrid Tea Rose. The varietal denomination of the new variety is 'WEKplagneze'. It has an undisseminated seedling of Applicant's creation as its seed parent and as its pollen parent the variety known as 'MACgenev' (U.S. Plant Pat. No. 8,279).

SUMMARY OF THE INVENTION

Among the features which distinguish the new variety from other presently available and commercial rose cultivars known to the inventor are the following combination of characteristics: its even coloration from the newly open stage to the three days old flower stage, its dark green very glossy foliage, its very upright growing habit, its somewhat inconspicuous receptacle, its many three leaflet leaves on the branches, its red suffusion on the rachis and the stipules, and its thornless branches and new shoots. The plant has a very upright growing habit, suitable for outdoor garden decoration.

Asexual reproduction of the new variety by budding as performed in Kern County and Upland, Calif., shows that the foregoing and other distinguishing characteristics come true to form and are established and transmitted through succeeding asexual propagations. 'WEKplagneze' may be asexually propagated by cuttings, budding or grafting.

COMPARISON WITH PARENTS

The new rose may be distinguished from its seed parent, 'MACgenev', an undessiminated seedling of Applicant's creation, by the following combination of characteristics: whereas 'WEKplagneze' bears double flowers with about 22 to 29 petals of pure white coloration which have a slight tea to fruity fragrance, the undisseminated seedling bears flowers of blended pink coloration with significantly higher petalage and a very strong rose fragrance. The new variety bears very dark green very glossy foliage, whereas the seed parent bears semi-glossy foliage of significantly lighter green coloration.

The new variety may be distinguished from its pollen parent, 'MACgenev' by the following combination of characteristics: whereas 'WEKplagneze' bears double flowers with about 22 to 29 petals of pure white coloration which have a slight tea to fruity fragrance, 'MACgenev' bears flowers of light pink coloration with significantly higher petalage and a very strong fragrance.

BRIEF DESCRIPTION OF ILLUSTRATION

The accompanying photograph illustrates specimens of the new variety and shows the flowering thereof from bud to full bloom depicted in color as nearly correct as it is possible to make in a color illustration of the character. Throughout this specification, color references and/or values are based upon The Colour Chart of The Royal Horticultural Society of London, England (1966), except where common terms of color definition are employed.

DESCRIPTION OF THE NEW VARIETY

The following description is of 3 to 4 year-old rose plants of the new variety grown outdoors in Upland, Calif. in the month of November. Phenotypic expression may vary with environmental, cultural and climatic conditions, as well as differences in conditions of light and soil.

BOTANICAL DESIGNATION

The new variety botanical designation is *Rosa hybrida* cv. 'WEKplagneze'.

FLOWER

The new variety usually bears its flowers singly. Flowers are borne on strong medium to long stems (about 45 to about 105 cms.). Outdoors, the plant blooms abundantly and nearly continuously during the growing season. The flowers have a slight tea to fruity fragrance.

BUD

The peduncle is about 4.8 to about 6.3 cms. in length, of somewhat heavy caliper (about 0.3 to about 0.5 cms. in diameter), usually erect and stiff. It is moderately smooth, with few stipitate glands and few hairs. Peduncle color is between 146B and 146A, often lightly suffused, especially on the side exposed to the sun, with between 183B and 183C.

Before the calyx breaks, the bud is about 1.4 to about 2.3 cms. in diameter at the widest point, about 1.8 to about 2.5 cms. in length, and pointed to moderately ovoid in shape with a moderately inconspicuous receptacle. The surface of the bud bears some foliaceous appendages, usually with somewhat stout cut foliaceous parts extending beyond the tip of the bud about ½ or more of its length. Bud color is between 137C and 146B sometimes lightly suffused, especially on the side exposed to the sun, with between 183B and 183C.

The sepals are about 2.5 to about 4.3 cms. in length and about 0.8 to about 1.2 cms. in width at the widest point. The outer surface color of the sepal is between 137C and 146B sometimes lightly suffused, especially on the side exposed to the sun, with between 183B and 183C. The inner surface color of the sepal is between 144A and 137B and covered with fine wooly tomentum; sepal margins are lined with many stipitate glands and hairs.

As the petals open (after the calyx breaks), the bud is about 2.3 to about 2.9 cms. in diameter at the widest point, about 2.5 to about 4.7 cms. in length, and pointed to somewhat ovoid in form. The color of the under and upper surfaces of the outermost newly opened petals is between 1A and 155A sometimes blushed, on the under surface, with as dark as between 187B and 71C. The color of the under and upper surfaces of the outermost newly opened petals is sometimes washed with between 144B and 145A. There is no visible change in coloration at the point where the petal attaches.

BLOOM

When fully open, the bloom ranges from about 10.8 to about 13.9 cms. in diameter. Petalage is double with about 22 to 29 petals and about 2 to 4 petaloids irregularly arranged. When partially open, the bloom form is high centered to somewhat globular, and the petals are moderately tightly spiraled to slightly cupped with petal edges moderately reflexed outward. When fully open, the bloom form is moderately cupped, and the petals are more cupped with petal edges moderately reflexed outward.

PETALS

The substance of the petals is moderately heavy and of medium thickness, with upper and under surfaces mostly matte to somewhat shiny. The outer petals are broadly rounded in shape with rounded apices. The inner petals are moderately rounded to broadly obovate in shape with rounded apices, sometimes slightly notched with one to two notches. The petals are about 5.2 to about 6.9 cms. in length and about 4.5 to about 5.8 cms. in width at the widest point. Petal margins are usually entire, sometimes slightly serrate.

NEWLY OPENED FLOWER

The under and upper surface color of the outer petals is between 155D and 155B sometimes lightly blushed on the outermost petals with as between 73B and 62D. At the point where the petal attaches, there is a moderately small zone of between 5D and 7D.

The under and upper surface color of the intermediate and inner petals is between 4D and 155B.

The general tonality of the newly opened flower is between 155D and 155B sometimes lightly blushed on the outermost petals with between 73B and 62D and between 4D and 155B toward the interior petals.

THREE DAY OLD FLOWER

The under and upper surface color of the outer and inner petals is between 155D and 155B sometimes lightly blushed on the outermost petals with as between 65A and 62D. At the point where the petal attaches, there is a moderately small zone of near 4D.

The general tonality of the three-day-old flower is between 155D and 155B sometimes lightly blushed on the outermost petals with between 65A and 62D.

On the spent bloom, the petals usually drop off cleanly.

In November in Upland, Calif., blooms on the bush growing outdoors generally last about four to five or more days. Cut roses from plants grown outdoors and kept at normal indoor living temperatures generally last about four to five or more days.

MALE REPRODUCTIVE ORGANS

Stamens are many in number (average about 100) and are arranged regularly about the pistils; a few are mixed with petaloids. The filaments are of moderately long length (about 0.7 to about 1.6 cms.), most with anthers. Filaments are near 5C at the base suffusing to between 11C and 9D in color and sometimes very lightly blushed with near 53C. The anthers are somewhat small to medium size for the class and all open approximately at the same time. Anther color is between 22B and 18D when immature and between 172A and 200B at maturity. Pollen is abundant.

FEMALE REPRODUCTIVE ORGANS

Pistils vary in number (average about 170). The styles are somewhat even, moderately short to average in length (about 0.3 to about 0.8 cms.), somewhat thin to average in caliper, and moderately bunched. Stigma color is between 20B and 22C. Style color is between 1D and 4D usually blushed with between 53D and 53C. Ovaries are usually all enclosed in the calyx.

Hips have not been observed on this variety when grown in Upland, Calif.

FOLIAGE

The compound leaves are usually comprised of many three to some five leaflets and are borne abundantly. The five-leaflet leaves are about 10.5 to about 12.7 cms. in length and about 10.2 to about 12.4 cms. in width at the widest point, moderately leathery to somewhat crisp in texture, and very glossy in finish. The terminal leaflets are about 5.7 to about 7.3 cms. in length and about 2.6 to about 4.9 cms. in width at the widest point, shaped moderately oval to ovate with very acute apices and round bases. Their margins are usually simply serrate.

The upper surface color of the mature leaf is darker than between 147A and 139A. The under surface color of the mature leaf is between 146B and 147B. The upper surface color of the young leaf is between 146A and 139A, usually heavily suffused with between 183B and 185A. The under surface color of the young leaf is between 147B and 148A, usually heavily suffused with between 183B and 185A.

The rachis is average in caliper and usually very smooth. The upper side is shallowly grooved with some hairs and few stipitate glands on the edges of the grooves. The under side of the rachis is usually very smooth but occasionally bears one to two small prickles, few hairs and stipitate glands. The rachis color is between 146B and 147B sometimes lightly suffused with between 187B and 185A.

The stipules are about 0.9 to about 1.3 cms. in length and moderately wide (about 0.6 to about 0.9 cms.) with somewhat short straight points that usually turn out at an angle of more than 45 degrees and sometimes recurve toward the stem. The stipule color is between 144A and 137B sometimes lightly suffused with between 187D and 185A.

The petiole is about 0.4 to about 0.8 cms. in length and about 0.1 to about 0.25 cms. in diameter at the widest point. The petiole color is between 146B and 147B.

The plant displays an above average degree of resistance to powdery mildew and rust as compared to other commercial varieties grown under comparable conditions in Upland, Calif. The plant's winter hardiness and drought/heat tolerance are yet to be determined.

GROWTH

The plant has a very upright medium height to somewhat tall growing habit (about 165 to about 225 cms. in height and about 88 to about 125 cms. spread at the widest point), with full branching. It displays moderately vigorous growth and the canes are of somewhat light to medium caliper for the class.

The color of the major stems is between 147B and 146A. They bear very few large prickles that are about 0.9 to about 1.4 cms. in length. The large prickles are almost straight and slightly angled downward with a somewhat short to medium length broad oval base; prickle color is between 177B and 165A. The major stem bears no small prickles.

The color of the branches is between 148B and 146A. They bear no large or small prickles.

The color of the new shoots is between 148B and 146B often heavily suffused with between 183A and 185A. They bear no large or small prickles.

I claim:

1. A new and distinct Hybrid Tea rose plant of the variety substantially as described and illustrated herein.

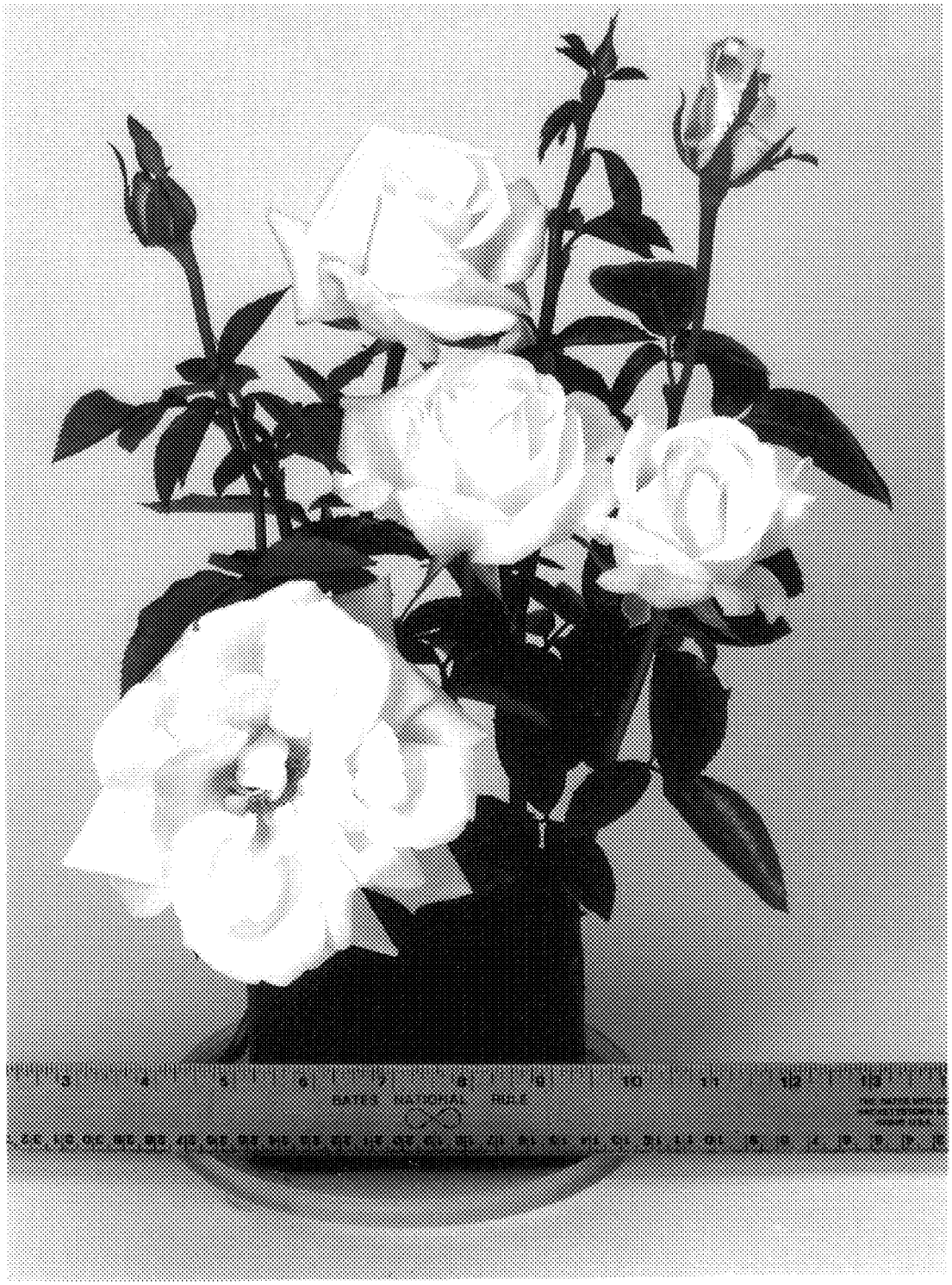

* * * * *